United States Patent [19]

Green

[11] 4,383,634

[45] May 17, 1983

[54] SURGICAL STAPLER APPARATUS WITH PIVOTALLY MOUNTED ACTUATOR ASSEMBLIES

[75] Inventor: David T. Green, Norwalk, Conn.

[73] Assignee: United States Surgical Corporation, Norwalk, Conn.

[21] Appl. No.: 267,080

[22] Filed: May 26, 1981

[51] Int. Cl.³ .............................................. A61B 17/04
[52] U.S. Cl. .................... 227/19; 128/334 R; 227/DIG. 1; 227/135; 227/155
[58] Field of Search ............. 128/334 R; 227/19, 135, 227/155, DIG. 1

[56] References Cited

U.S. PATENT DOCUMENTS

| | | | |
|---|---|---|---|
| 2,344,071 | 3/1944 | Wilson et al. | 1/49.1 |
| 3,017,637 | 1/1962 | Sampson | 1/50 |
| 3,080,564 | 3/1963 | Strekopitov et al. | 1/50 |
| 3,252,643 | 5/1966 | Strekopytov et al. | 227/109 |
| 3,269,630 | 8/1966 | Fleischer | 227/107 |
| 3,275,211 | 9/1966 | Hirsch et al. | 227/124 |
| 3,315,863 | 4/1967 | O'Dea | 227/19 |
| 3,494,533 | 2/1970 | Green et al. | 227/19 |
| 3,519,187 | 7/1970 | Kapitanov et al. | 227/19 |
| 3,589,589 | 6/1971 | Akopov | 227/153 |
| 3,692,224 | 9/1972 | Astafiev et al. | 227/19 |
| 3,795,034 | 3/1974 | Strekopytov et al. | 29/212 D |
| 3,935,981 | 2/1976 | Akopov et al. | 227/19 |
| 4,111,206 | 9/1978 | Vishnevsky et al. | 128/305 |
| 4,204,623 | 5/1980 | Green | 227/19 |
| 4,216,891 | 8/1980 | Behlke | 227/30 |

FOREIGN PATENT DOCUMENTS

| | | |
|---|---|---|
| 406832 | 12/1924 | Fed. Rep. of Germany . |
| 906791 | 9/1962 | United Kingdom . |
| 1276239 | 6/1972 | United Kingdom . |

Primary Examiner—Paul A. Bell
Attorney, Agent, or Firm—Robert R. Jackson; John E. Nathan

[57] ABSTRACT

Surgical stapler apparatus in which the actuator elements can be pivoted out of the actuator housing to facilitate cleaning of the apparatus between uses without disassembly of the apparatus.

22 Claims, 14 Drawing Figures

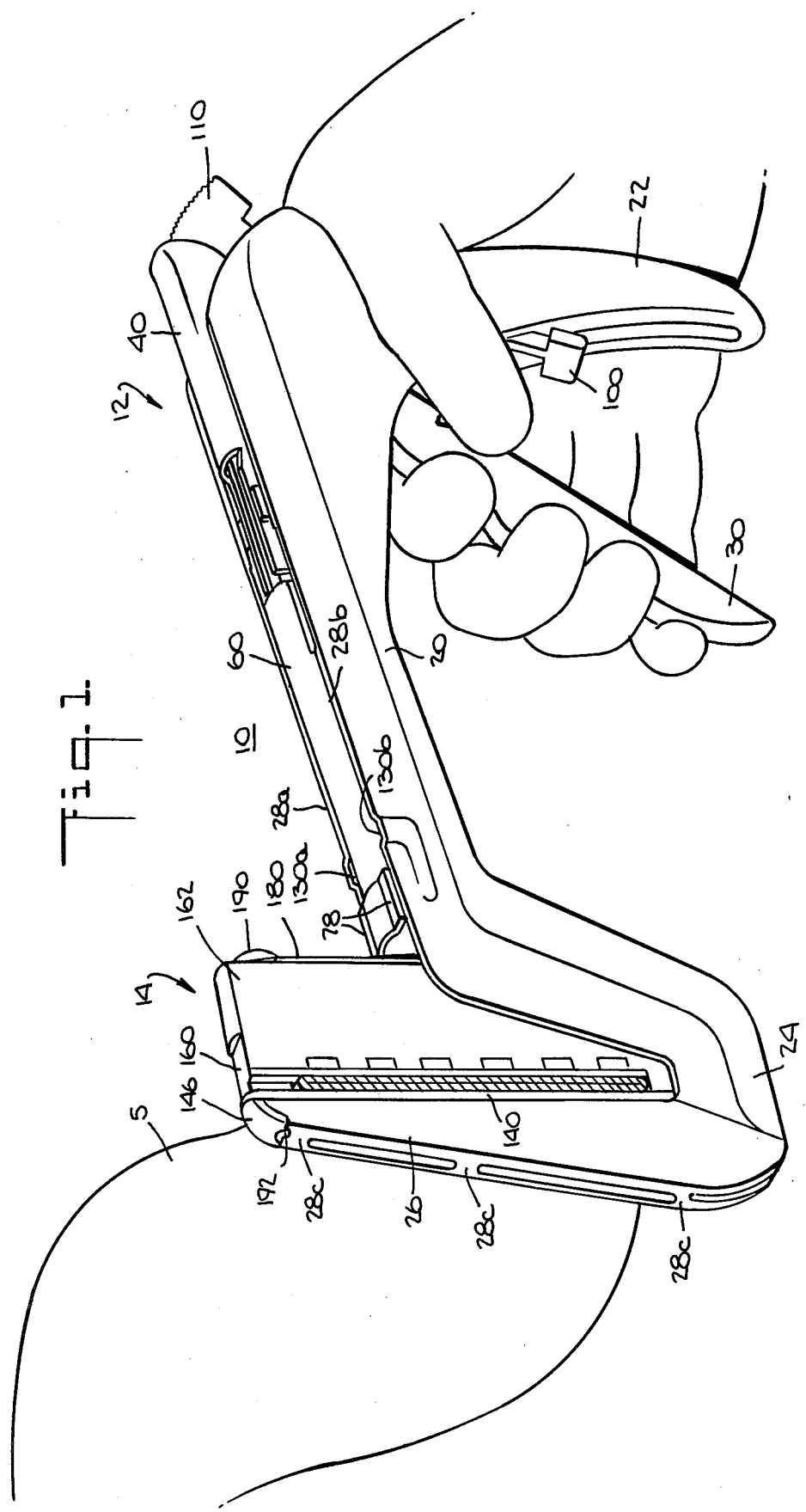

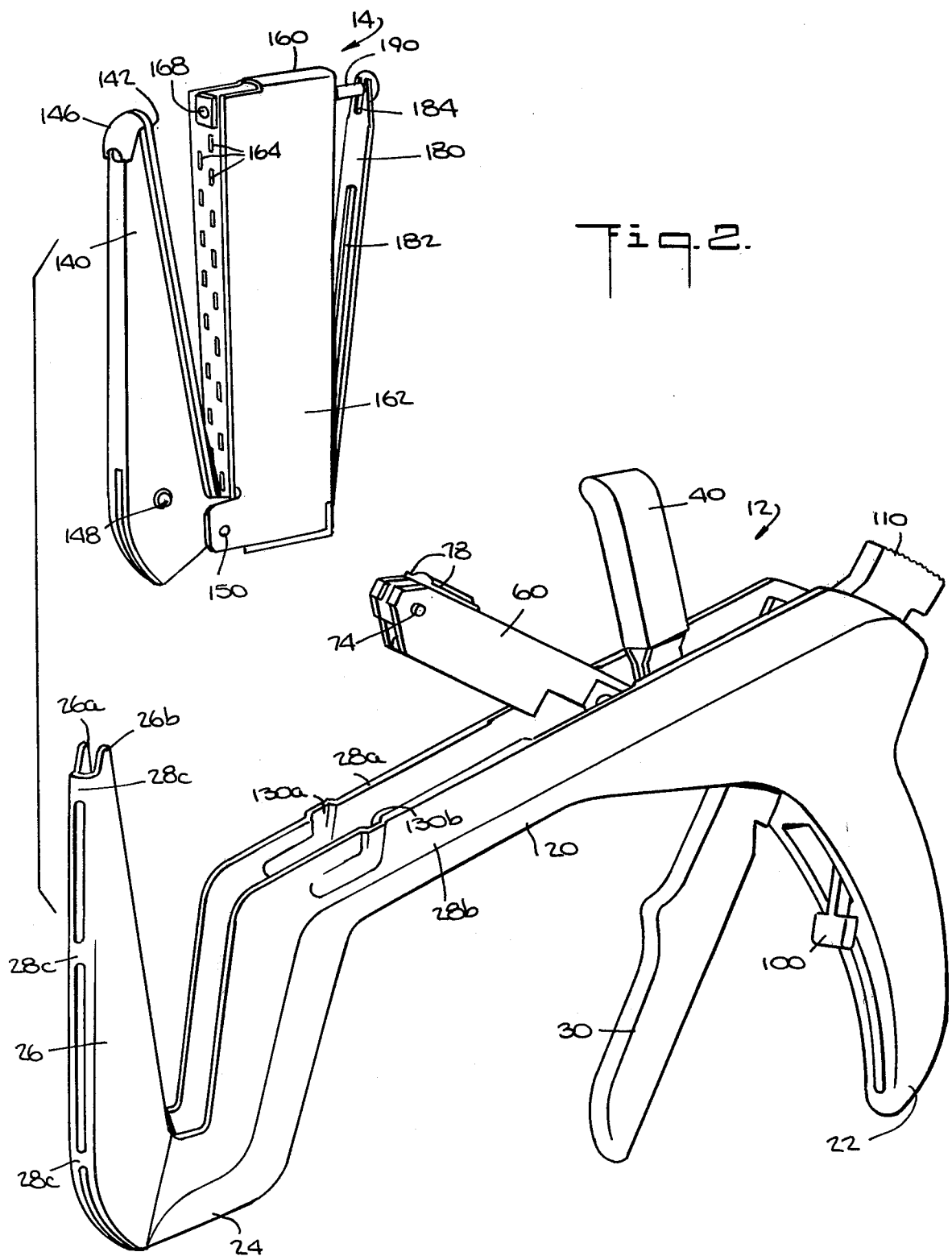

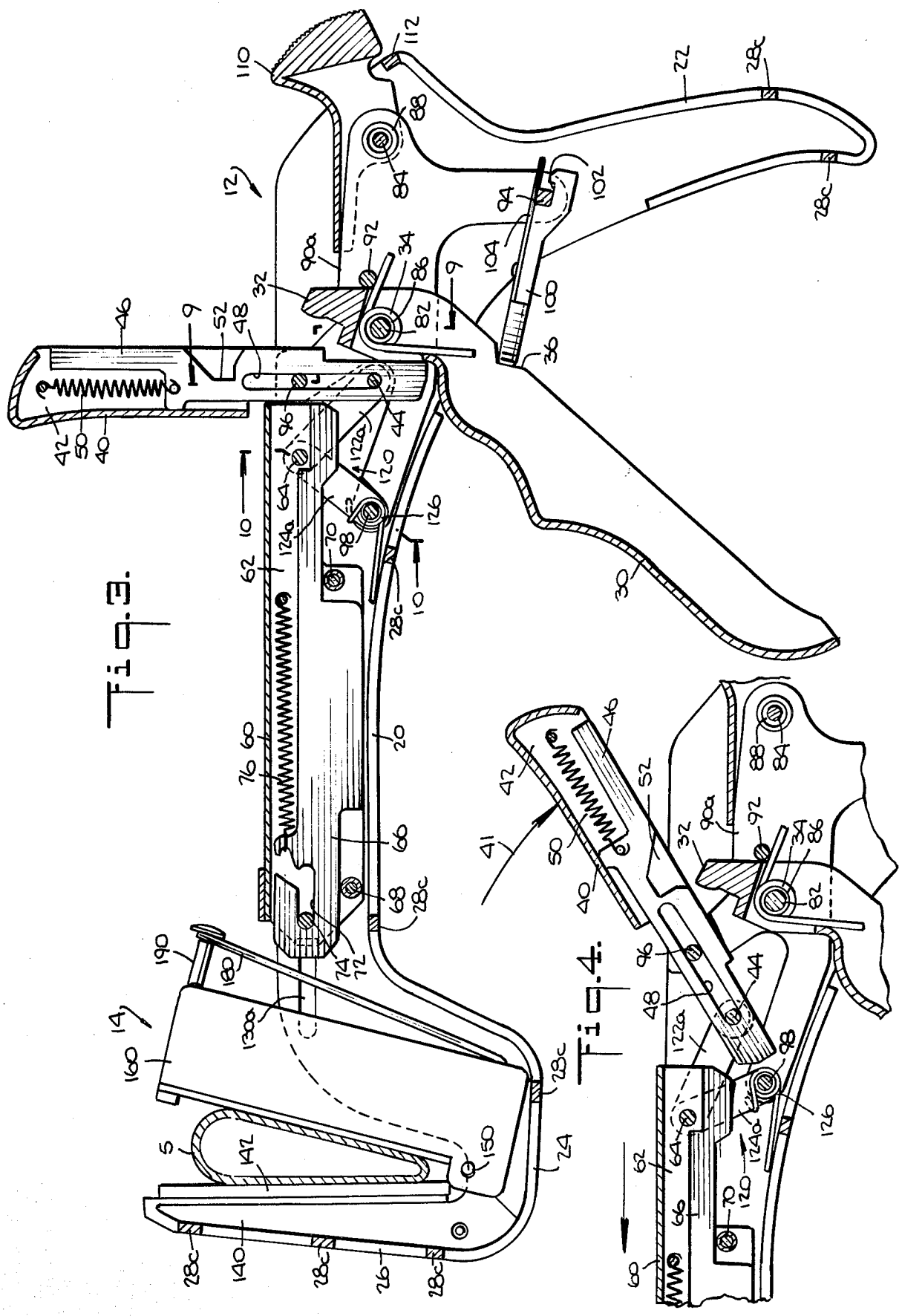

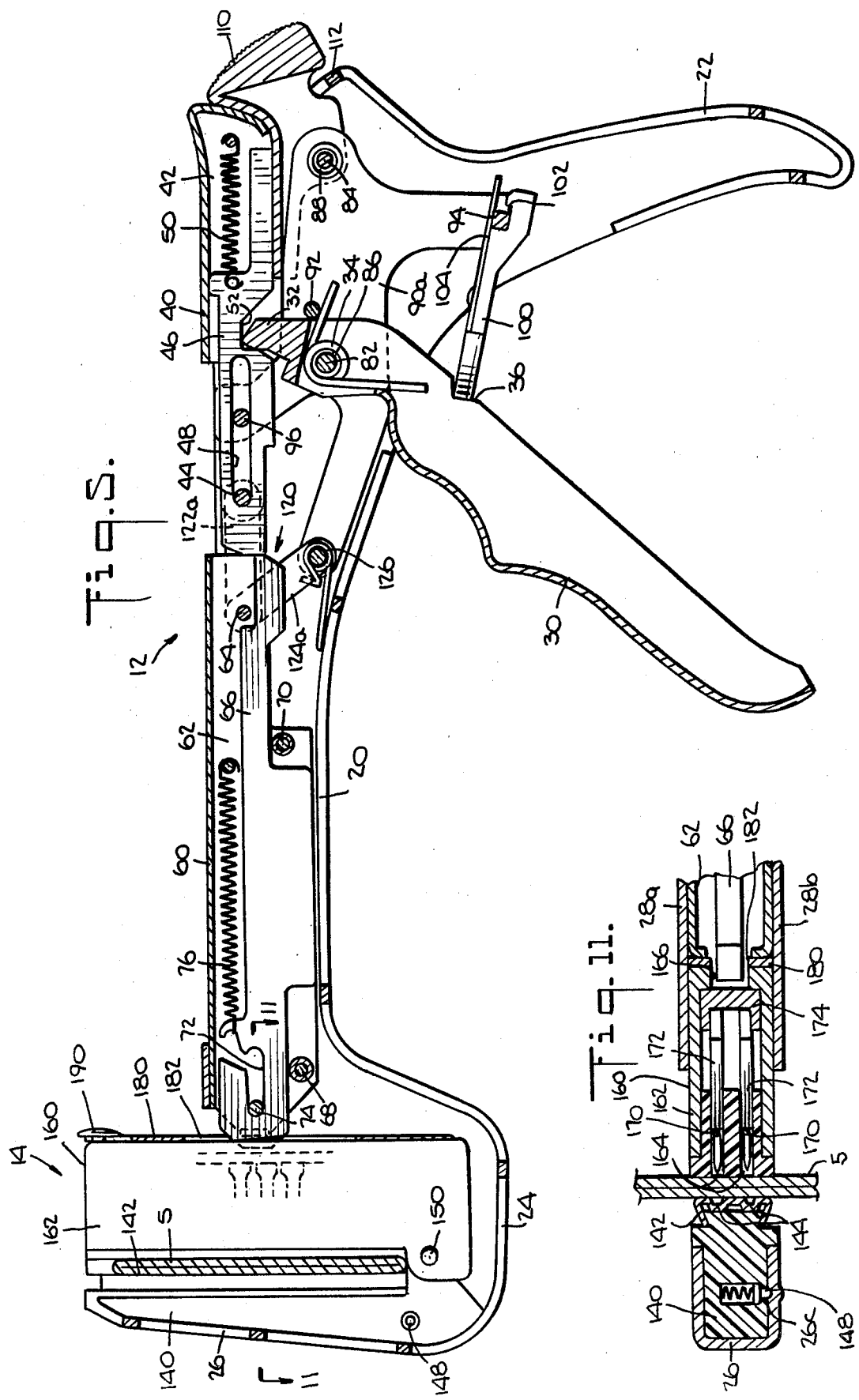

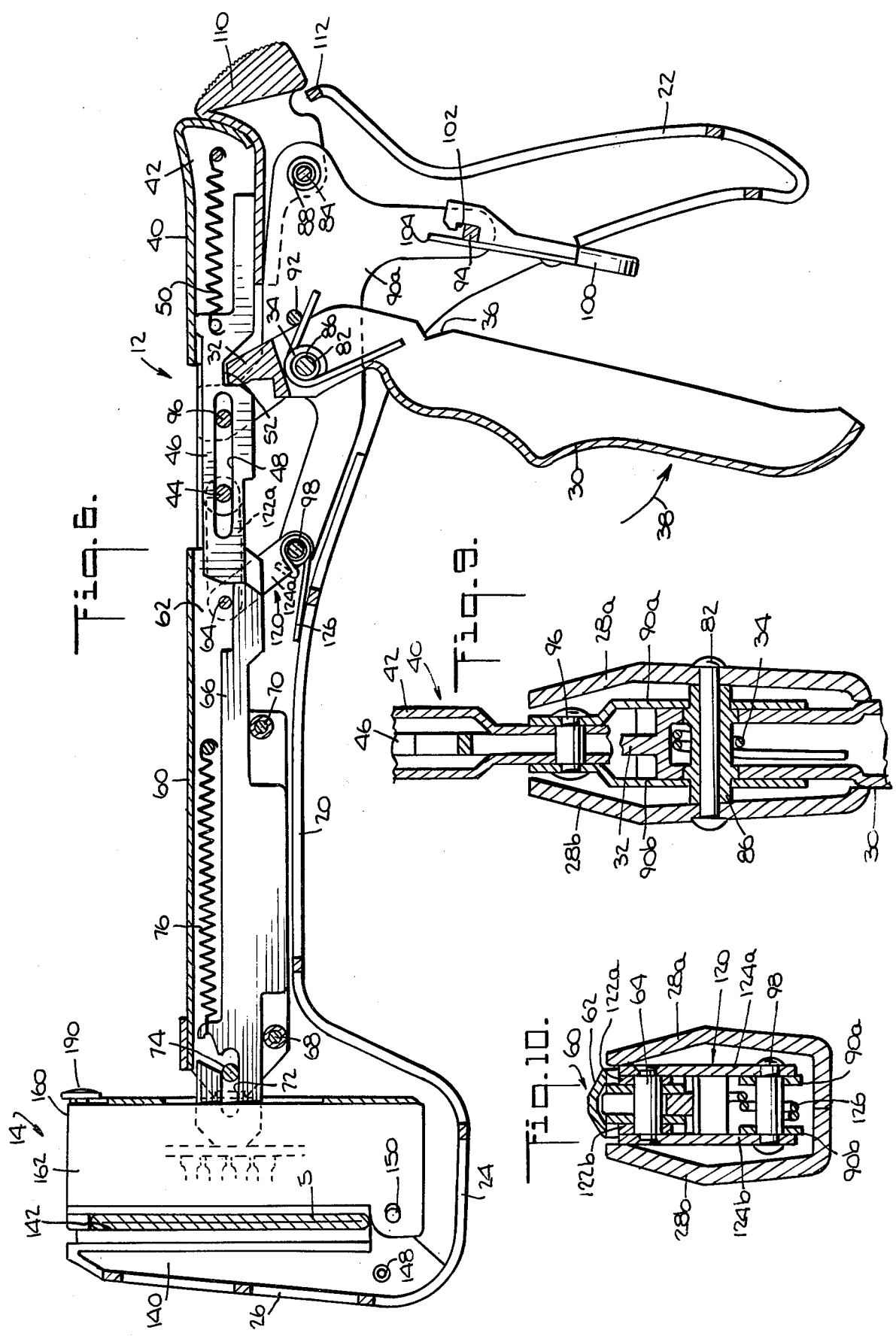

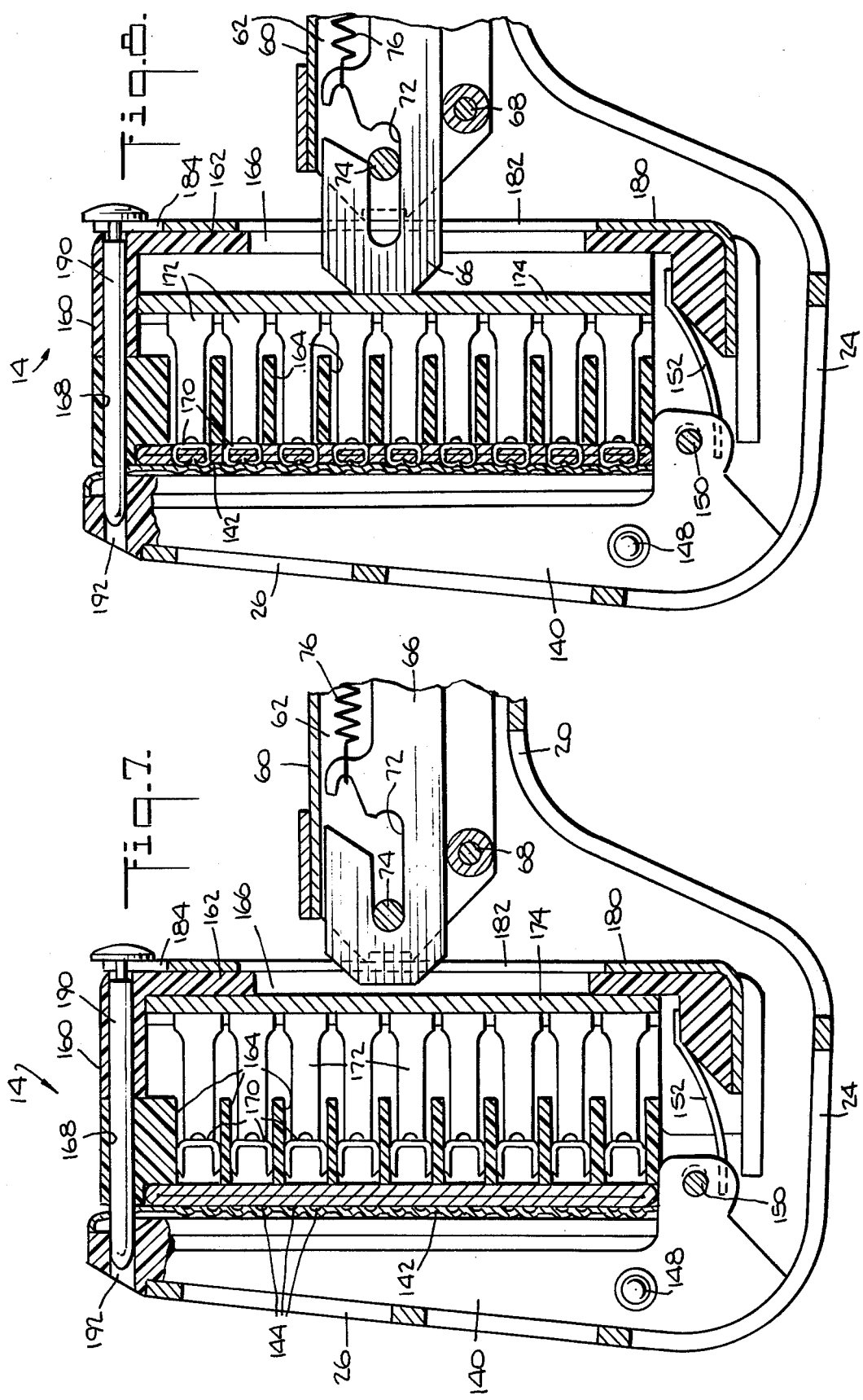

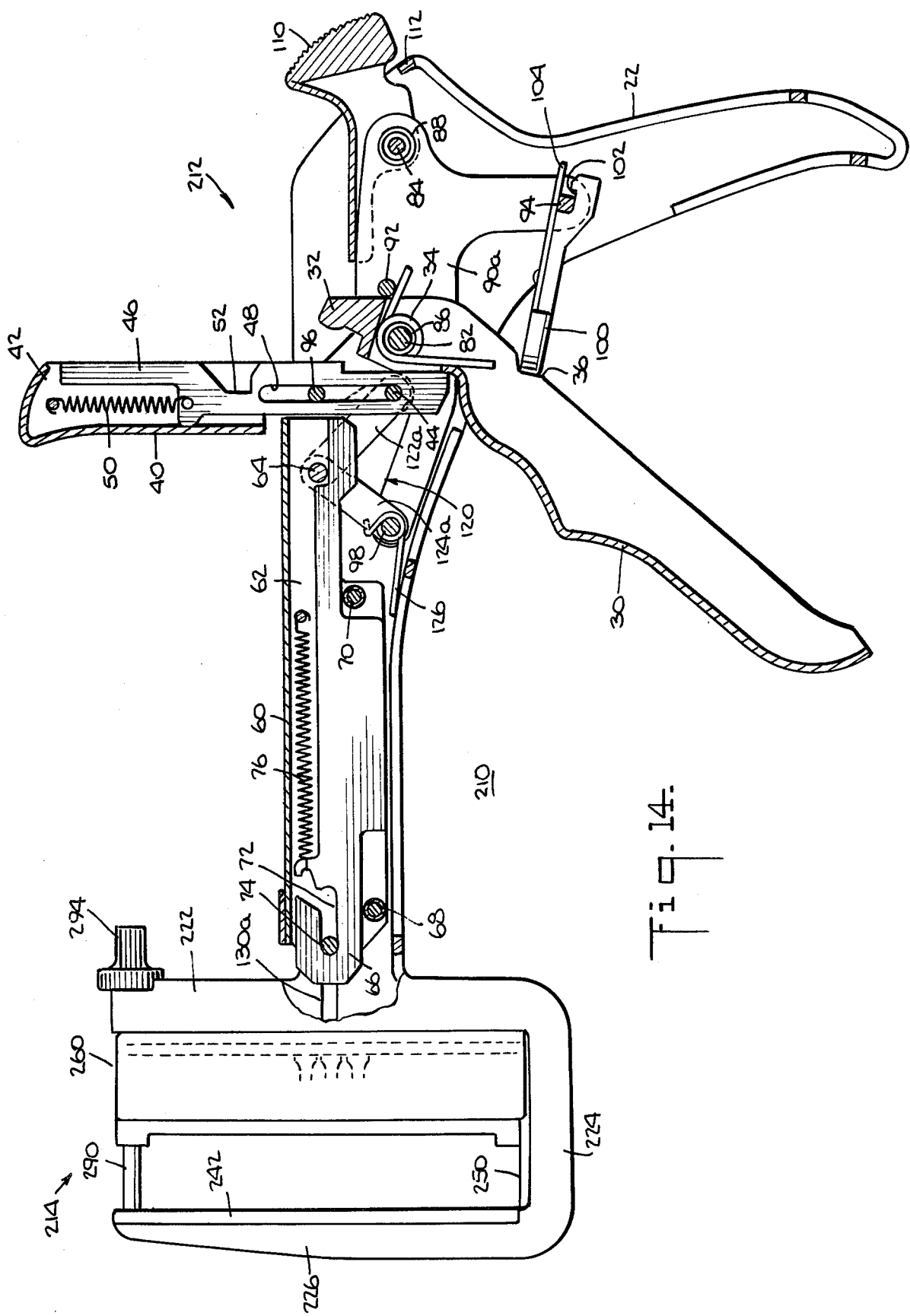

SURGICAL STAPLER APPARATUS WITH PIVOTALLY MOUNTED ACTUATOR ASSEMBLIES

BACKGROUND OF THE INVENTION

This invention relates to surgical stapler apparatus, and more particularly to surgical stapler apparatus which can be readily cleaned between uses without disassembly of the parts of the apparatus.

Surgical staplers are known in which the actuator is permanent and reusable (as distinguished from disposable after a single use or after use in a single surgical procedure), and in which the actuator removably receives a disposable staple cartridge. Although the disposable staple cartridge is replaced when the apparatus is to be reused, the permanent actuator must be cleaned and sterilized between uses. Cleaning the actuator can be a time-consuming process.

Most permanent surgical stapler actuators are designed for at least partial disassembly to facilitate cleaning of the apparatus. Surgical staplers are typically precision instruments with substantial numbers of closely fitting moving parts. Coagulable body fluids and other materials to which these instruments are exposed during surgical procedures can get into the apparatus and interfere with subsequent operation unless completely removed. At least partial disassembly of the instrument is therefore typically required to permit cleaning of interior parts and interior clearances of the apparatus.

To the extent that any disassembly of such an instrument is required, the maintenance of the instrument is made more complex and the risk of damage to the instrument during maintenance is increased. The disassembled parts of the instrument may be more delicate than the fully assembled device, and these parts may therefore be more easily damaged than the instrument as a whole. The disassembled parts may also be subject to loss. And the instrument may be damaged by improper reassembly.

In view of the foregoing, it is an object of this invention to improve and simplify surgical staplers, particularly those having permanent parts which must be cleaned between uses.

It is a more particular object of this invention to provide improved surgical staplers which do not require any disassembly for cleaning between uses.

SUMMARY OF THE INVENTION

These and other objects of the invention are accomplished in accordance with the principles of the invention by providing surgical staplers in which the actuator assembly or assemblies are pivotable out of the frame of the apparatus to permit access to all parts of the apparatus without disassembly of any portion of the apparatus.

Further features of the invention, its nature and various advantages will be more apparent from the accompanying drawing and the following detailed description of the invention.

BRIEF DESCRIPTION OF THE DRAWING

FIG. 1 is a perspective view of a first illustrative embodiment of surgical stapler apparatus constructed in accordance with the principles of this invention, and showing that apparatus in use to staple tissue.

FIG. 2 is a perspective view of the apparatus of FIG. 1 showing the actuator separate from the staple cartridge.

FIG. 3 is an elevational view, partly in section, of the apparatus of FIG. 1.

FIGS. 4-6 and 12 are views similar to FIG. 3 showing successive stages in the operation of the apparatus.

FIG. 7 is a detailed elevational section of a portion of the apparatus of FIG. 1.

FIG. 8 is a view similar to FIG. 7 showing a subsequent stage in the operation of the apparatus.

FIG. 9 is a cross sectional view taken along the line 9—9 in FIG. 3.

FIG. 10 is a cross sectional view taken along the line 10—10 in FIG. 3.

FIG. 11 is a cross sectional view taken along the line 11—11 in FIG. 5.

FIG. 14 is an elevational view, partly in section, of a second illustrative embodiment of surgical stapler apparatus constructed in accordance with the principles of this invention.

DETAILED DESCRIPTION OF THE INVENTION

Figure 12:
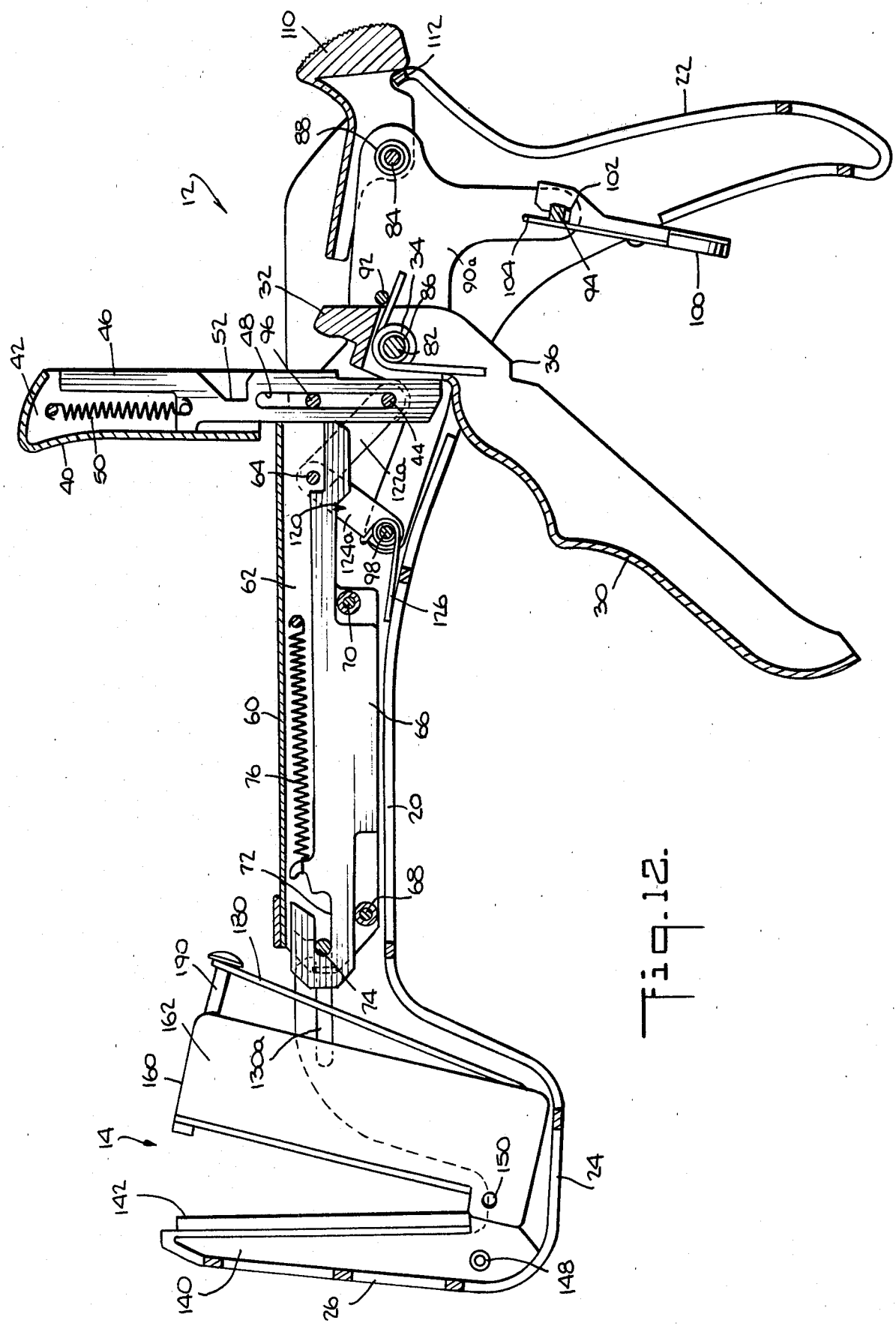

Although the principles of the invention are applicable to other types of surgical staplers, the invention will be fully understood from an explanation of its application to the type of surgical staplers known as linear closure staplers. Similarly, although one of the important advantages of the invention is that it facilitates cleaning of permanent surgical stapler apparatus, the invention also has other advantages which can make it useful for instruments which are designed to be disposable after use in a single surgical procedure and which therefore do not require cleaning. Thus the invention is not limited to permanent instruments.

I. First Illustrative Embodiment:

Linear Closure Stapler with Pivoting Staple Cartridge

A. Overall Construction and Operation

A first illustrative embodiment of the invention is shown in FIGS. 1-13. As shown, for example, in FIG. 1, this embodiment is a linear closure surgical stapler 10 having a permanent and reusable actuator 12, on which a disposable, pivoting stapling assembly or cartridge 14 is removably mounted. Staple cartridge 14 and actuator 12 are shown separated from one another in FIG. 2. Staple cartridge 14 may be substantially identical to the corresponding portion of the apparatus shown in applicant's co-pending U.S. patent application Ser. No. 188,691, filed Sept. 29, 1980, which is hereby incorporated by reference herein. As can be seen in FIG. 2, staple cartridge 14 includes an anvil supporting member 140, on which staple holding assembly 160 is pivotally mounted by means of pin 150.

Actuator 12 includes a rigid frame or housing 20 having a fixed handle 22 at its proximal end and a U-shaped portion 24 at its distal end. Staple cartridge 14 is removably mountable on the distal leg 26 of the U-shaped portion of frame 20 by engagement of anvil holding member 140 in distal leg 26. When thus mounted on actuator 12, staple holding assembly 160 of cartridge 14 is freely movable between the two spaced side members 28a and 28b of frame 20 so that the staple holding assembly can continue to pivot about pin 150 in the cartridge.

Movable handle 30 is pivotally mounted on frame 20 adjacent fixed handle 22 so that it can be operated by the fingers of the hand holding handle 22 (see FIG. 1). Two actuator assemblies, generally identified by the reference numbers 40 and 60, are pivotally mounted within frame 20 between spaced side members 28a and 28b. In FIG. 2 actuator assemblies 40 and 60 are shown fully pivoted out from the top of frame 20, and in FIG. 1 actuator assemblies 40 and 60 are shown fully pivoted into or parallel to the longitudinal axis of frame 20.

As will be discussed in greater detail below, when a staple cartridge 14 is mounted on frame 20 and actuator assemblies 40 and 60 are positioned as shown, for example, in FIG. 3 (i.e., with distal actuator assembly 60 parallel to the longitudinal axis of the frame and with proximal actuator assembly 40 perpendicular to the longitudinal axis of the frame), staple holding assembly 160 is pivoted clockwise as viewed in the Figures away from anvil suppporting member 140 so that tissue 5 to be stapled can be placed between anvil supporting member 140 and staple holding assembly 160. Thereafter, pivoting of proximal actuator assembly 40 from the position shown in FIG. 3 to the position shown in FIG. 5 causes distal actuator assembly 60 to translate as a whole in the distal direction. The distal end of actuator assembly 60 contacts leaf spring 180 on cartridge 14, and leaf spring 180 in turn contacts the proximal side of staple holding assembly 160, thereby pivoting staple holding assembly 160 counter-clockwise as viewed in the Figures about pin 150. As shown in FIG. 5, the counter-clockwise pivoting of staple holding assembly 160 clamps the tissue to be stapled between the distal face of staple holding assembly 160 and anvil 142, which is mounted on the proximal side of anvil supporting member 140.

When actuator assembly 40 is fully pivoted into alignment with the longitudinal axis of frame 20 as shown in FIG. 5, staple holding assembly 160 is parallel to anvil 142, and the apparatus is then ready to staple the tissue. The staples are driven by pivoting movable handle 30 toward fixed handle 22 as shown in FIG. 6. This causes staple pusher actuator members 46 and 66, which are respectively mounted in actuator assemblies 40 and 60, to move in the distal direction so that the distal end of member 66 enters staple holding assembly 160 and actuates the staple driving elements in that assembly. Staples are thereby driven from staple holding assembly 160, through tissue 5, and against anvil 142 (see FIG. 8). Anvil 142 clinches the ends of the staples so that the staples will remain in and secure the tissue.

When the staples have been driven, handle 30 is released and staple pusher actuator members 46 and 66 return to their initial proximal positions. The apparatus is removed from the stapled tissue by pivoting proximal actuator assembly 40 out from frame 20 with the aid of actuator release lever 110 as shown in FIG. 12. This retracts distal actuator assembly 60 to its original proximal position and allows cartridge 14 to open and release the stapled tissue. The instrument can then be removed from the tissue.

B. Detailed Construction of the Actuator

As mentioned above and as shown, for example, in FIGS. 1 and 2, actuator frame 20 includes substantially parallel, spaced side members 28a and 28b. Side members 28a and 28b are rigidly and preferably permanently connected together by such means as tabs 28c (FIGS. 1-3) along portions of the periphery of side members 28a and 28b, and by pins or rivets 82 and 84 (FIGS. 3-6 and 9) extending transversely through the actuator at fixed pivotal axes in the apparatus. Inside actuator frame 20, each of rivets 82 and 84 is surrounded by an annular collar 86 and 88, respectively. Collar 86 is typical of both of these collars and is shown in detail in FIG. 9. Collars 86 and 88 help maintain the proper spacing between side members 28a and 28b, and also support other elements in the actuator.

Among the elements mounted on collars 86 and 88 are two parallel spaced mounting plates 90a and 90b, best seen, for example, in FIGS. 3 and 9. Mounting plates 90a and 90b are substantially similar to one another, one plate being the mirror image of the other. Mounting plates 90a and 90b are fixed relative to actuator frame 20 by virtue of being mounted on both of collars 86 and 88.

Between mounting plates 90a and 90b movable handle 30 is pivotally mounted on collar 86. As shown, for example, in FIG. 3, handle 30 is resiliently biased clockwise by coil spring 34 around collar 86. One straight end of coil spring 34 bears against handle 30 below the pivotal axis defined by rivet 82, while the other straight end of coil spring 34 bears against stop 92 on one or both of support plates 90a and 90b. The clockwise pivoting of handle 30 is stopped by contact of the portion of handle 30 above pivotal axis 82 with stop 92.

Inadvertent operation of handle 30 is prevented by safety latch 100, which is pivotally mounted on shaft 94 extending between support plates 90a and 90b (see, for example, FIG. 3). As shown in FIG. 3, safety latch 100 is initially rotated clockwise so that the distal end of the latch engages notch 36 in handle 30, thereby preventing handle 30 from being pivoted counter-clockwise. When it is desired to operate handle 30, safety latch 100 must first be pivoted counter-clockwise out of engagement with handle 30, as shown, for example, in FIG. 6. Safety latch 100 seeks either the latching position shown in FIG. 3 or the unlatched position shown in FIG. 6 as a result of cooperation between substantially square shaft 94, enlarged square notch 102 in latch 100, and leaf spring 104 on latch 100.

As can be seen, for example, in FIGS. 3 and 9, proximal actuator assembly 40 includes a channel-like support member or housing 42 which is pivotally mounted on pin or rivet 96. Pin 96 extends between support plates 90a and 90b. Another pin or rivet 44 passes through housing 42 parallel to pin 96 and pivotally connects housing 42 to the proximal ends of the proximal links 122a and 122b of linkage 120. As described in detail below, linkage 120 operatively connects proximal actuator assembly 40 to distal actuator assembly 60. Proximal staple pusher actuator member 46 is reciprocally mounted in housing 42 by means of pins 44 and 96 passing through elongated slot 48 in member 46. Member 46 is resiliently biased toward the proximal end of housing 42 by tension coil spring 50 which is connected between housing 42 and member 46. The bottom of housing 42 is open to allow tongue 32 on movable handle 30 to enter notch 52 in member 46 when proximal actuator assembly 40 is pivoted parallel to the actuator, as shown, for example, in FIG. 5.

As can be seen, for example, in FIGS. 3 and 10, distal actuator assembly 60 also includes a channel-like support member or housing 62 which is pivotally mounted on pin or rivet 64. Pin 64 extends transversely through housing 62 near the proximal end of housing 62 parallel to pins 44 and 96. Pin 64 forms the intermediate hinge connection in linkage 120. Linkage 120 includes a proximal link (made up of two substantially identical, parallel, spaced link members 122a and 122b) and a distal link (made up of two substantially identical, parallel, spaced link members 124a and 124b). The proximal ends of link members 122a and 122b are pivotally connected to pin 44 as described above. The distal ends of link members 122a and 122b and the proximal ends of link members 124a and 124b are pivotally connected by pin 64. And the distal ends of link members 124a and 124b are pivotally connected to rivet or pin 98, which extends parallel to pin 64 between support plates 90a and 90b. The location of pin 98 is therefore fixed relative to actuator frame 20, while pins 44 and 64 are movable within actuator frame 20 as described in more detail below. Coil spring 126 is mounted on pin 98 so as to resiliently pivot link member 124a clockwise about pin 98. The effect of spring 126 is to resiliently bias linkage 120, and therefore distal actuator assembly 60, in the proximal direction.

Distal staple pusher actuator member 66 is reciprocally mounted in housing 62 by resting on pins 68 and 70, which extend transversely in housing 62 below member 66. Member 66 also has an elongated slot 72 for allowing actuator restraint pin 74 (described in more detail below) to extend transversely through actuator assembly 60 without interfering with the reciprocal motion of member 66 relative to the remainder of assembly 60. Member 66 is resiliently biased in the proximal direction in housing 62 by tension coil spring 76 which extends between housing 62 and member 66. Accordingly, the distal end of slot 72 initially contacts pin 74.

As shown in FIG. 2, the two opposite ends of actuator restraint pin 74 project from opposite sides of housing 62. These ends of pin 74 form lugs on each side of distal actuator assembly 60 near the distal end of that assembly. When distal actuator assembly 60 is pivoted into actuator frame 20, these lugs fit into L-shaped channels 130a and 130b, which are formed, respectively, in actuator frame side members 28a and 28b. Channels 130a and 130b are located relative to pin 74 so that when proximal actuator assembly 40 is pivoted out from actuator frame 20, the ends of pin 74 are aligned with the vertical legs of channels 130a and 130b. Accordingly, pin 74 and channels 130a and 130b do not then prevent actuator assembly 60 from being pivoted out of actuator frame 20 about pivotal axis 64 as shown, for example, in FIGS. 2 or 13. However, when distal actuator assembly 60 has been pivoted into alignment with actuator frame 20 and proximal actuator assembly 40 also begins to be pivoted into alignment with actuator frame 20, the entire distal actuator assembly 60 translates in the distal direction relative to frame 20 and the ends of pin 74 enter the legs of channels 130a and 130b which are aligned with the longitudinal axis of actuator 12. This prevents inadvertent pivoting of assembly 60 about pivotal axis 64 except when distal actuator assembly 60 is in its most proximal position.

Near the proximal end of actuator 12, release lever 110 is pivotally mounted on pivotal axis 84. Release lever 110 is pivotable between the position shown, for example, in FIG. 3 (in which the distal portion of release lever 110 rests on mounting plates 90a and 90b) and the position shown in FIG. 12 (in which the proximal portion of release lever 110 bears on stop 112 on actuator frame 20). If desired, release lever 110 may be resiliently biased to pivot counter-clockwise as viewed in the Figures by any conventional spring arrangement (not shown). The purpose of release lever 110 is to facilitate release of proximal actuator assembly 40 after the staples have been driven and when it is desired to remove the instrument from the stapled tissue. Accordingly, in the normal position shown, for example, in FIG. 5, the distal upper surface of release lever 110 allows proximal actuator assembly 40 to pivot parallel to the longitudinal axis of actuator 12; and when thus pivoted, proximal actuator assembly 40 comes to rest against the distal upper surface of release lever 110. When it is desired to pivot proximal actuator assembly 40 out of actuator 12 again, release lever 110 is pivoted clockwise as shown in FIG. 12. The distal end of release lever 110 then presses up on the bottom of proximal actuator assembly 40 and initiates counter-clockwise pivoting of that assembly about pivotal axis 96. Once initiated by release lever 110, counter-clockwise pivoting of proximal actuator assembly 40 tends to continue in respose to the urging of spring 126 acting through linkage 120.

C. Detailed Construction of the Staple Cartridge

As mentioned above, staple cartridge 14 (shown separate from actuator 12 in FIG. 2) may be substantially identical to the corresponding part of the apparatus shown in applicant's co-pending U.S. patent application Ser. No. 188,691, filed Sept. 29, 1980. Accordingly, staple cartridge 14 will be described herein only to the extent necessary to facilitate an understanding of the present invention.

As seen, for example, in FIGS. 2 and 3, the two main parts of staple cartridge 14 are anvil supporting member 140 and staple holding assembly 160. Assembly 160 is pivotally mounted on member 140 by means of pin 150. Staple clinching anvil 142 (best seen in FIGS. 7, 8, and 11) is mounted on the proximal side of member 140. In the particular embodiment shown in the drawing, anvil 142 includes two parallel rows of staple clinching depressions or pockets 144. When staple holding assembly 160 is pivoted parallel to anvil 142, as best seen, for example, in FIG. 7, a staple clinching pocket 144 is opposite each end of each of staples 170 in staple holding assembly 160.

The distal side of anvil supporting member 140 is shaped to fit into and be supported by the distal leg 26 of actuator frame 20, as shown, for example, in FIGS. 1 and 11. Anvil supporting member 140 has a cap 146 (FIG. 2) adapted to fit over and engage points 26a and 26b on the free ends of distal frame leg 26. Springloaded detent member 148 (FIGS. 2 and 11) is also mounted on anvil supporting member 140 for releasably engaging depression 26c in distal frame leg 26. Elements 146 and 148 and the complementary portions of distal frame leg 26 cooperate to retain anvil supporting member 140 in the proper position on actuator frame 20, while allowing ready removal of cartridge 14 from the actuator when desired.

As shown, for example, in FIGS. 2 and 7, staple holding assembly 160 includes rigid housing 162 having two parallel spaced rows of staple holding channels 164 which open out on the distal side of assembly 160. As shown in FIGS. 7 and 11, each staple holding channel 164 initially contains a generally U-shaped staple 170 oriented so that the pointed ends of the staple legs point in the distal direction. The back of each of staples 170 is contacted by a staple pusher 172, and the proximal ends of all of staple pushers 172 are contacted by transverse staple pusher member 174. Transverse staple pusher member 174 is accessible to the staple pusher actuator elements of actuator 12 via elongated slot 166 in the proximal side of housing 162.

As can be seen, for example, in FIG. 7, leaf spring 152 is mounted on a portion of anvil supporting member 140 and bears on an interior surface of housing 162. Leaf spring 152 resiliently pivots staple holding assembly 160 clockwise about pivotal axis 150 so that cartridge 14 is normally open to receive tissue as shown, for example, in FIG. 3.

As can be seen in FIGS. 2, 3, and 7, the lower end of leaf spring 180 is mounted on the bottom of housing 162 so that the major portion of spring 180 is adjacent to, but resiliently biased away from, the proximal surface of housing 162. Leaf spring 180 has an elongated slot 182 which is approximately co-extensive with slot 166 in housing 162. Adjacent its upper end, spring 180 has another open-ended slot 184, best seen in FIG. 2, which engages the distal end of alignment pin 190.

Alignment pin 190 is reciprocally mounted in aperture 168 (FIG. 7) which extends through the top of housing 162. The purpose of alignment pin 190 is to help make sure that staple holding assembly 160 is properly aligned with anvil 142 when cartridge 14 is closed and the tissue is about to be stapled. In order to accomplish this, when cartridge 14 is being closed, actuator 12 first presses leaf spring 180 against the proximal surface of housing 162 in the manner more fully described below. This causes the distal end of alignment pin 190 to extend from the distal end of aperture 168. As cartridge 14 continues to close, staple holding assembly 160 pivots toward anvil supporting member 140 and the projecting distal end of alignment pin 190 enters aperture 192 (FIG. 7) in the upper end of anvil 142 and anvil supporting member 140. Alignment of staple holding assembly 160 and anvil 142 for proper clinching of staples 170 by anvil 142 is thereby assured.

D. Detailed Operation

Considering now the detailed operation of surgical stapler 10, the typical initial condition of the apparatus is shown in FIG. 3. In that condition, movable handle 30 is held against inadvertent operation by safety latch 100. Also in that condition, proximal actuator assembly 40 is pivoted out substantially perpendicular to the longitudinal axis of actuator 12, while distal actuator assembly 60 is aligned with the longitudinal axis of the actuator and fully retracted in the proximal direction. Staple cartridge 14 is mounted on the actuator by means of anvil supporting member 140. Because distal actuator assembly 60 is retracted proximally, staple holding assembly 160 of cartridge 14 pivots clockwise to allow the cartridge to be placed around the tissue 5 to be stapled.

When tissue 5 has been properly positioned in the apparatus, proximal actuator assembly 40 is pivoted clockwise about fixed pivotal axis 96 by manual pressure on housing 42 as represented by the arrow 41 in FIG. 4. This causes pivotal axis 44 to move clockwise in an arc about pivotal axis 96. Link members 122a and 122b respond to this motion of pivotal axis 44 by driving pivotal axis 64 in a counter-clockwise arc about fixed pivotal axis 98, to which movable pivotal axis 64 is tied by link members 124a and 124b. As pivotal axis 64 moves, it drives distal actuator assembly 60 in the distal direction. Distal staple pusher actuator member 66 is carried with the remainder of assembly 60 by contact of the distal end of slot 72 with pin 74.

As distal actuator assembly 60 moves distally in response to the clockwise pivoting of proximal actuator assembly 40, the distal end of housing 62 contacts the proximal surface of leaf spring 180 on both sides of elongated slot 182 (FIGS. 2 and 11). The force thus applied to leaf spring 180 by distal actuator assembly 60 causes spring 180 to deflect until it is substantially parallel to and in contact with the proximal surface of staple holding assembly 160. Thereafter, continued distal motion of distal actuator assembly 60 causes staple holding assembly 160 to pivot counter-clockwise about pivotal axis 150. As staple holding assembly 160 pivots toward anvil 142, the tissue 5 to be stapled is gradually clamped between the distal face of staple holding assembly 160 and anvil 142. Deflection of spring 180 parallel to the proximal surface of housing 162 also causes the distal end of alignment pin 190 to project from the distal side of housing 162 so that that end of pin 190 will enter aperture 192 in anvil 142 and anvil supporting member 140 when cartridge 14 is closed.

It should be noted that as the clamping of the tissue between staple holding assembly 160 and anvil 142 becomes tighter, the mechanical advantage of linkage 120 increases so that the relatively large force required to securely clamp the tissue can be produced in response to relatively small force applied to pivot proximal actuator assembly 40. The mechanical advantage of linkage 120 increases as the angle between proximal actuator housing 42 and links 122a and 122b approaches 180°. It should also be noted that the entire actuator transmits tissue clamping force to staple holding assembly 160 very efficiently because the amount of lateral motion between leaf spring 180 and the distal end of distal actuator assembly 60 is relatively small. This is due to the substantially linear motion of distal actuator assembly 60 toward staple holding assembly 160. Accordingly, the distal end of distal actuator assembly 60 does not wipe an extended portion of the length of leaf spring 180 during the course of closing staple cartridge 14 to clamp the tissue. As a consequence, only a relatively small amount of energy is expended in overcoming frictional forces between those elements.

When proximal actuator assembly 40 has been pivoted parallel to the longitudinal axis of actuator 12 as shown in FIG. 5, the pivotal connection 44 between assembly 40 and links 122a and 122b is slightly over center, i.e., links 122a and 122b slope downward slightly in the distal direction. (The downward slope of links 122a and 122b is too slight to be visible in the Figures.) This effectively latches proximal actuator assembly 40 down in the position shown in FIG. 5 so that it does not pivot counter-clockwise in response to the proximally directed forces acting on it through linkage 120. Also, when proximal actuator assembly 40 is parallel to actuator 12, staple holding assembly 160 is substantially parallel to anvil 142, with tissue 5 firmly clamped therebetween (see also FIG. 11). Tongue 32 on the upper end of movable handle 30 extends into notch 52 in proximal staple pusher actuator member 46. The distal end of member 46 is aligned with the proximal end of distal staple pusher actuator member 66. And, as is best seen in FIGS. 7 and 11, the distal end of member 66 extends through slot 182 in leaf spring 180 and into slot 166 in staple holding assembly 160 adjacent the proximal surface of transverse staple pusher member 174. The apparatus is therefore ready to staple the tissue.

When the tissue is to be stapled, safety latch 100 is pivoted down to the position shown in FIG. 6, thereby releasing handle 30. To drive the staples, handle 30 is manually pivoted counter-clockwise as shown by the arrow 38 in FIG. 6. This causes tongue 32 on the upper end of handle 30 to drive proximal staple pusher actuator member 46 in the distal direction. The distal end of member 46 contacts the proximal end of distal staple pusher actuator member 66, thereby driving member 66 in the distal direction also. As best seen in FIG. 8, the distal end of member 66 in turn contacts the proximal side of transverse staple pusher member 174 in staple holding assembly 160 and drives member 174 in the distal direction. The distal motion of transverse staple pusher member 174 drives all of staple pushers 172 in the distal direction, thereby driving all of staples 170 from staple holding assembly 160, through tissue 5, and against anvil 142, which clinches the ends of the staples to secure them in the tissue. Stapling of the tissue is now complete.

As soon as the tissue has been stapled as described above, handle 30 can be released. Spring 34 automatically returns handle 30 to its initial position, shown, for example, in FIG. 5. This allows springs 50 and 76 to respectively retract proximal and distal staple pusher actuator members 46 and 66 to their initial proximal positions, also shown, for example, in FIG. 5. However, the stapled tissue remains clamped in staple cartridge 14.

To release the stapled tissue from cartridge 14, release lever 110 is manually pivoted clockwise as shown in FIG. 12. This causes proximal actuator assembly 40 to pivot counter-clockwise about fixed pivotal axis 96. Once counter-clockwise pivoting of assembly 40 has been thus initiated, it tends to continue in response to the clockwise rotational force exerted on link member 124a by spring 126. Accordingly, assembly 40 continues to pivot counter-clockwise until stopped by contact with the proximal end of distal actuator assembly 60 when assembly 40 is substantially perpendicular to the longitudinal axis of actuator 12 as shown in FIG. 12. During the above-described counter-clockwise pivoting of assembly 40, linkage 120 operates to retract distal actuator assembly 60 in the proximal direction. This allows staple cartridge 14 to re-open as shown in FIG. 12 so that the instrument can be removed from the stapled tissue.

If the apparatus is to be used again in the same surgical procedure, safety latch 100 is re-engaged with handle 30 and expended staple cartridge 14 is removed and replaced by a new staple cartridge. The instrument is then ready for re-use.

Between surgical procedures, actuator 12 must be thoroughly cleaned and sterilized. Staple cartridges 14, being preferably disposable, are not re-used and thus do not require cleaning or sterilization by the user. Actuator 12 is therefore cleaned and sterilized without a staple cartridge being present, and a staple cartridge is typically mounted on the actuator only when it is about to be used.

Figure 13:
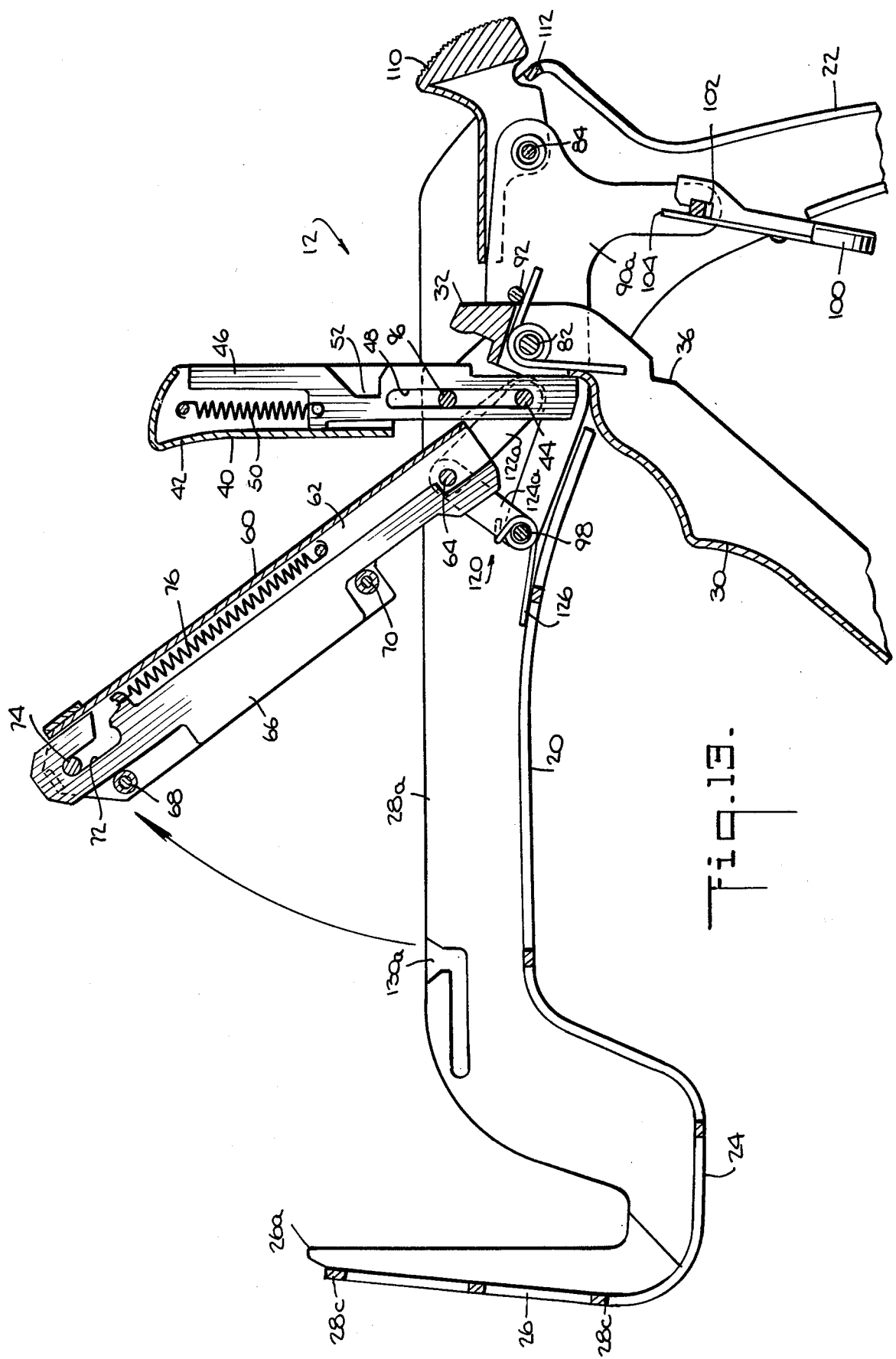
FIG. 13 is a view similar to FIG. 3 showing the actuator without the staple cartridge and as configured to facilitate cleaning.

To facilitate cleaning of actuator 12, both of proximal and distal actuator assemblies 40 and 60 are pivotable out of actuator frame 20 as shown in FIGS. 2 and 13. When proximal actuator assembly 40 is pivoted substantially perpendicular to the longitudinal axis of actuator 12, distal actuator assembly 60 is retracted proximally so that the lugs formed by the ends of pin 74 are aligned with the vertical legs of L-shaped channels 130a and 130b. Accordingly, distal actuator assembly 60 can then be pivoted clockwise out of actuator frame 20 to the position shown in FIG. 13. Laterally extending tabs 78 (FIGS. 1 and 2) near the distal end of assembly 60 enable the user to grasp assembly 60 for pivoting out in this manner. The outward pivoting of assembly 60 stops when the proximal end of housing 62 contacts links 122a and 122b as shown in FIG. 13.

Because both of actuator assemblies 40 and 60 are pivotable out from actuator frame 20, all of the moving parts of the actuator are exposed for cleaning, with no disassembly of any portion of the apparatus being required. The undersides of both of housings 42 and 62 are open so that both of reciprocating staple pusher actuator members 46 and 66 are exposed for cleaning. This is especially important for distal actuator assembly 60, which is closest to the stapling site and which is therefore most likely to become contaminated with material such as tissue fragments, blood, and other body fluids. Linkage 120 is also substantially exposed for cleaning when assemblies 40 and 60 are pivoted out. Accordingly, the entire actuator can be thoroughly cleaned without removing any parts from the actuator. This greatly speeds and otherwise facilitates the cleaning operation. It also eliminates the possibility that loose parts may be lost or improperly reassembled. And it substantially reduces the possibility of damage to the individual parts during the cleaning operation.

When the instrument has been cleaned and sterilized, distal actuator assembly 60 can be pivoted parallel to the longitudinal axis of actuator 12 once again as shown in any of the Figures other than 2 and 13. The instrument is ready for use in a surgical procedure as soon as a staple cartridge 14 is loaded on the actuator.

II. Second Illustrative Embodiment:

Linear Closure Stapler with Translating Staple Cartridge

FIG. 14 shows how the principles of this invention can be applied to another type of linear closure surgical stapler, i.e., a linear closure stapler 210 in which the staple holding assembly 260 translates rather than pivots relative to anvil 242. Actuator 212 is substantially identical to actuator 12 in the first embodiment described above, except that the distal end portion 224 of the actuator frame is adapted to receive a somewhat different type of staple cartridge 214. In particular, the staple cartridge in this embodiment may be functionally similar to the corresponding portion of the apparatus shown and described in Green et al. U.S. Pat. No. 3,494,533, which is hereby incorporated by reference herein.

Staple cartridge 214 includes anvil 242 and staple holding assembly 260. Anvil 242 is slideable on and off distal frame leg 226 via the upper free end of leg 226. Staple holding assembly 260 is reciprocally mounted on the actuator frame by means of rail 250 along the bottom of the distal portion 224 of the frame, and by means of removable alignment pin 290, which extends through the upper portion of staple holding assembly 260 and is secured in the adjacent ends of both legs of the frame. The distal end of pin 290 is preferably threaded into the upper end of distal frame leg 226 to securely retain the pin during the clamping and stapling of the tissue. The proximal end of pin 290 includes knurled knob 294 to facilitate fastening and unfastening pin 290. Proximal frame leg 222 has a passageway through it to allow the distal end of distal actuator assembly 60 (similar to the correspondingly designated portion of the actuator in the first embodiment) to pass through the proximal frame leg and actuate staple holding assembly 260 as described below.

The remainder of actuator 212 may be substantially identical to actuator 12 in the above-described first embodiment. Thus the same reference numbers are applied in FIG. 14 as were used in FIGS. 1–13 to designate portions of the FIG. 14 apparatus which are identical to the correspondingly designated portions of the apparatus of FIGS. 1–13.

Operation of the FIG. 14 apparatus is generally similar to operation of the first embodiment. After the tissue to be stapled is positioned between anvil 242 and staple holding assembly 260, pin 290 is threaded into the end of distal frame leg 226. Proximal actuator assembly 40 is then pivoted clockwise until it is parallel to the longitudinal axis of the actuator. This causes distal actuator assembly 60 to translate in the distal direction so that the distal end of assembly 60 passes through the aperture in proximal frame leg 222 and drives staple holding assembly 260 in the distal direction until the tissue to be stapled is clamped between anvil 242 and the distal face of assembly 260. The tissue is stapled by first releasing safety latch 100, and then pivoting handle 30 counter-clockwise. As in the first embodiment, this causes distal staple pusher actuator member 66 to translate in the distal direction. The distal end of member 66 enters the proximal side of staple holding assembly 260 and causes the staple pusher elements (not shown) in that assembly to drive the staples from that assembly, through the clamped tissue, and against anvil 242, which clinches the ends of the staples.

When the tissue has thus been stapled, handle 30 is released and release lever 110 is pivoted clockwise to release proximal actuator assembly 40. Assembly 40 then pivots counter-clockwise and distal actuator assembly 60 retracts in the proximal direction. This releases the clamping force on expended staple holding assembly 260. Pin 290 is then released and retracted so that the apparatus can be removed from the stapled tissue.

Distal actuator assembly 60 in FIG. 14 is pivotable out of actuator 212 in the same way that corresponding assembly 60 in the first embodiment is pivotable out of the actuator in that embodiment (see FIGS. 2 and 13). Accordingly, the actuator of the second embodiment can also be thoroughly cleaned between uses without disassembly of any portion of the actuator.

I claim:

1. Surgical stapling apparatus comprising:
   a frame for supporting a stapling assembly adjacent a distal portion of the frame;
   a first actuator means pivotally mounted relative to a proximal portion of the frame, the first actuator means being pivotable away from the frame sufficiently to allow cleaning of both the first actuator means and the frame without removal of the first actuator means from the frame;
   a second actuator means mounted relative to the frame for both pivotal and reciprocal motion and located intermediate the first actuator means and the stapling assembly, the second actuator means being pivotable away from the frame sufficiently to allow cleaning of both the second actuator means and the frame without removal of the second actuator means from the frame; and
   means for interconnecting the first and second actuator means so that the second actuator means responds to pivoting of the first actuator means by translating toward the stapling assembly and at least partially actuating the stapling assembly.

2. Surgical stapling apparatus comprising:
   a frame, having proximal and distal portions and a longitudinal axis which passes through both the proximal and distal portions, for supporting a tissue clamping and stapling assembly adjacent the distal portion;
   a first actuator means pivotally mounted relative to the proximal portion about a first pivotal axis which is transverse to the longitudinal axis of the frame;
   a second actuator means mounted relative to the frame for both pivotal and reciprocal motion and located intermediate the first actuator means and the stapling assembly, the second actuator means being pivotal about a second pivotal axis which is transverse to the longitudinal axis of the frame, the second actuator means including a reciprocally mounted actuator member;
   means for interconnecting the first and second actuator means so that the second actuator means responds to pivoting of the first actuator means by translating toward the tissue clamping and stapling assembly to actuate the tissue clamping and stapling assembly to clamp the tissue in preparation for subsequent stapling of the clamped tissue; and
   means for translating the actuator member toward the tissue clamping and stapling assembly after the second actuator means has been translated toward the tissue clamping and stapling assembly to actuate the tissue clamping and stapling assembly to staple the clamped tissue.

3. The apparatus defined in claim 1 wherein the means for translating the actuator member toward the tissue clamping and stapling assembly comprises:
   a further actuator member reciprocally mounted in the first actuator means for contacting the actuator member in the second actuator means when the first actuator means has been pivoted to cause translation of the second actuator means toward the tissue clamping and stapling assembly; and
   means for translating the further actuator member toward the second actuator means to cause the actuator member in the second actuator means to translate toward the tissue clamping and stapling assembly.

4. The apparatus defined in claim 3 wherein the means for translating the further actuator member comprises a handle pivotally mounted on the frame for engaging the further actuator member when the first actuator means has been pivoted to cause translation of the second actuator means toward the tissue clamping and stapling assembly.

5. The apparatus defined in claim 1 further comprising means for preventing pivoting of the second actuator means except when the second actuator means is fully retracted from the tissue clamping and stapling assembly.

6. The apparatus defined in claim 1 wherein the means for interconnecting the first and second actuator means comprises linkage means for providing increasing mechanical advantage as the second actuator means translates toward the tissue clamping and stapling assembly.

7. For use in combination with a surgical stapling assembly containing at least one surgical staple, an actuator comprising:

a frame for supporting the stapling assembly;

a first actuator assembly mounted relative to the frame for pivotal motion toward and away from the frame to expose the parts of the actuator for cleaning when the first actuator assembly is pivoted away from the frame, the first actuator assembly including a first housing and a first staple pusher actuator member reciprocally mounted in the first housing;

a second actuator assembly including a second housing and a second staple pusher actuator member reciprocally mounted in the second housing;

linkage means operatively connecting the first and second actuator assemblies for translating the second actuator assembly toward the stapling assembly to actuate the stapling assembly to clamp the tissue to be stapled in response to pivoting of the first actuator assembly;

means for pivotally mounting the second actuator assembly relative to the linkage means so that the second actuator assembly can be pivoted toward and away from the frame to expose the parts of the actuator for cleaning when the second actuator assembly is pivoted away from the frame; and means for causing the first and second staple pusher actuator members to translate in the direction of the stapling assembly to actuate the stapling assembly to drive the staple from the stapling assembly to staple the tissue.

8. The apparatus defined in claim 7 wherein the linkage means comprises:

a first link member pivotally connected adjacent one end to the first actuator assembly at a point intermediate the pivotal axis of the first actuator assembly and the second actuator assembly, and pivotally connected adjacent the opposite second end to the second actuator assembly; and a second link member pivotally connected adjacent one end to the pivotal connection between the first link member and the second actuator member, and pivotally connected adjacent the opposite second end to the frame.

9. The apparatus defined in claim 8 wherein the linkage means further comprises means for increasing the mechanical advantage of the linkage means as the second actuator assembly advances toward the stapling assembly.

10. The apparatus defined in claim 7 wherein the means for causing the first and second staple pusher actuator members to translate includes means for operatively engaging the first and second staple pusher actuator members only when the first actuator assembly has been pivoted to cause the tissue to be clamped.

11. The apparatus defined in claim 7 wherein the means for causing the first and second staple pusher actuator members to translate comprises an actuator handle pivotally mounted relative to the frame and having a portion which can contact the first staple pusher actuator member only when the first actuator assembly has been pivoted to cause the tissue to be clamped.

12. The apparatus defined in claim 11 further comprising a safety latch for preventing the actuator handle from pivoting prior to release of the safety latch.

13. The apparatus defined in claim 7 further comprising means for preventing pivoting of the second actuator assembly relative to the frame unless the second actuator assembly is substantially retracted from the stapling assembly.

14. The apparatus defined in claim 7 further comprising means for resiliently biasing the second actuator assembly away from the stapling assembly.

15. The apparatus defined in claim 7 wherein the first and second staple pusher actuator members are resiliently biased away from the stapling assembly.

16. A surgical stapler comprising:

a frame;

a stapling assembly removably mounted on a distal portion of the frame, the stapling assembly including an anvil portion and a staple holding portion pivotally mounted on the proximal side of the anvil portion;

first actuator means pivotally mounted relative to the frame proximally of the stapling assembly;

second actuator means disposed intermediate the first actuator means and the stapling assembly;

linkage means operatively interconnecting the first and second actuator means so that pivoting of the first actuator means causes translation of the second actuator means in the direction of the stapling assembly, which causes the staple holding portion to pivot toward the anvil portion and clamp the tissue to be stapled between the staple holding portion and the anvil portion;

means for causing the second actuator means to actuate the staple holding portion to drive the staples from the staple holding portion, through the clamped tissue, and against the anvil portion so that the ends of the staples are clinched; and means for pivotally mounting the second actuator means relative to the frame.

17. The apparatus defined in claim 16 wherein the first actuator means comprises a first actuator support member pivotally mounted relative to the frame and a first staple pusher actuator member reciprocally mounted relative to the first actuator support member, and wherein the second actuator means comprises a second actuator support member pivotally mounted relative to the linkage means and a second staple pusher actuator member reciprocally mounted relative to the second actuator support member.

18. The apparatus defined in claim 17 wherein the reciprocal axes of the first and second staple pusher actuator members are aligned when the first actuator means is pivoted so that the second actuator means is translated in the direction of the staple holding portion.

19. The apparatus defined in claim 18 wherein the linkage means comprises:

a first link member pivotally connected adjacent a first end to a portion of the first actuator support member intermediate the pivotal axis of the first actuator means and the second actuator means, and pivotally connected adjacent the other second end to the second actuator support member; and a second link member pivotally connected adjacent a first end to the pivotal connection adjacent the second end of the first link member, and pivotally connected adjacent the other second end to the frame.

20. The apparatus defined in claim 18 wherein the means for causing the second actuator means to actuate the staple holding portion to drive the staples comprises a handle pivotally mounted relative to the frame for engaging the first staple pusher actuator member when the first actuator member is pivoted so that the second actuator means is translated in the direction of the stapling assembly, pivoting of the handle when thus engaged with the first staple pusher actuator member causing the first staple pusher actuator member to translate in the direction of the stapling assembly so that the second staple pusher actuator member also translates in the direction of the stapling assembly and actuates the staple holding portion to drive the staples.

21. The apparatus defined in claim 16 further comprising means for preventing pivoting of the second actuator means when the second actuator means is translated in the direction of the stapling assembly.

22. The apparatus defined in claim 16 wherein the mechanical advantage of the linkage means increases as the second actuator means translates toward the stapling assembly.

* * * * *